United States Patent
Wolf

(10) Patent No.: US 10,098,741 B2
(45) Date of Patent: Oct. 16, 2018

(54) PENILE PROSTHETIC WITH AN INSERTION SLEEVE ATTACHABLE TO AN INFLATABLE BLADDER

(71) Applicant: Coloplast A/S, Humlebaek (DK)

(72) Inventor: Donald Wolf, Shoreview, MN (US)

(73) Assignee: Coloplast A/S, Humlebaek (DK)

( * ) Notice: Subject to any disclaimer, the term of this patent is extended or adjusted under 35 U.S.C. 154(b) by 47 days.

(21) Appl. No.: 15/281,123

(22) Filed: Sep. 30, 2016

(65) Prior Publication Data
US 2017/0086976 A1    Mar. 30, 2017

Related U.S. Application Data

(60) Provisional application No. 62/234,665, filed on Sep. 30, 2015.

(51) Int. Cl.
*A61F 5/00*    (2006.01)
*A61F 2/26*    (2006.01)

(52) U.S. Cl.
CPC ........ *A61F 2/26* (2013.01); *A61F 2210/0004* (2013.01); *A61F 2250/0018* (2013.01); *A61F 2250/0019* (2013.01)

(58) Field of Classification Search
CPC .......................................................... A61F 2/26
USPC ...................................................... 600/38–41
See application file for complete search history.

(56) References Cited

U.S. PATENT DOCUMENTS

| | | | |
|---|---|---|---|
| 1,410,296 A | 3/1922 | Hannah | |
| 3,722,104 A | 3/1973 | Enzetti | |
| 4,244,370 A | 1/1981 | Furlow et al. | |
| 4,318,396 A * | 3/1982 | Finney | A61F 2/26 600/40 |
| 4,350,151 A | 9/1982 | Scott | |
| 4,590,927 A | 5/1986 | Porter et al. | |
| 4,602,621 A | 7/1986 | Hakky | |
| 4,611,584 A | 9/1986 | Finney | |
| 4,628,912 A | 12/1986 | Fischell | |
| 4,653,485 A | 3/1987 | Fishell | |
| 4,904,183 A | 2/1990 | Hannan et al. | |
| 5,010,882 A | 4/1991 | Polyak et al. | |
| 5,056,223 A | 10/1991 | Buck et al. | |
| 5,088,925 A | 2/1992 | Mason | |
| 5,167,611 A | 12/1992 | Cowan | |
| 5,281,230 A | 1/1994 | Heidmueller | |
| 5,484,450 A | 1/1996 | Mohamed | |

(Continued)

FOREIGN PATENT DOCUMENTS

| | | |
|---|---|---|
| CN | 2059828 U | 8/1990 |
| CN | 2093615 U | 1/1992 |

(Continued)

*Primary Examiner* — John Lacyk

(74) *Attorney, Agent, or Firm* — Coloplast Corp., Coloplast A/S; Nick Baumann

(57) ABSTRACT

A penile prosthetic includes a penile implant sized for insertion into a dilated corpora cavernosum of a penis and an insertion sleeve. The penile implant includes a proximal tip that is insertable into a crus penis and an inflatable bladder connected to the proximal tip. The inflatable bladder has a first column strength and includes a distal tip that is insertable into a glans penis. The insertion sleeve is attachable to an outside surface of the inflatable bladder. The insertion sleeve is soluble in saline or water.

12 Claims, 6 Drawing Sheets

(56) References Cited

U.S. PATENT DOCUMENTS

| | | |
|---|---|---|
| 5,968,067 A | 10/1999 | Mooreville et al. |
| 6,679,832 B1 | 1/2004 | Sultan |
| 6,808,489 B2 | 10/2004 | George et al. |
| 7,066,878 B2 | 6/2006 | Eid |
| 7,169,103 B2 | 1/2007 | Ling et al. |
| 7,172,602 B2 | 2/2007 | George et al. |
| 7,390,296 B2 * | 6/2008 | Mische ............. A61F 2/26 600/40 |
| 7,942,808 B1 * | 5/2011 | Morningstar ....... A61F 2/26 600/40 |
| 9,333,079 B2 | 5/2016 | Daniel |
| 9,345,575 B2 * | 5/2016 | Daniel ............... A61F 2/26 |
| 9,855,144 B2 * | 1/2018 | Kubalak ............. A61F 2/26 |
| 2002/0193659 A1 | 12/2002 | Yachia et al. |
| 2003/0220539 A1 | 11/2003 | George et al. |
| 2003/0220540 A1 | 11/2003 | Kuyava |
| 2004/0010244 A1 | 1/2004 | George et al. |
| 2004/0215056 A1 | 10/2004 | Ling et al. |
| 2004/0225182 A1 | 11/2004 | Eid |
| 2007/0175487 A1 | 8/2007 | Eid |
| 2007/0283969 A1 | 12/2007 | Yamasaki et al. |
| 2009/0132044 A1 | 5/2009 | George et al. |
| 2009/0137867 A1 | 5/2009 | Goto |
| 2009/0182289 A1 | 7/2009 | List et al. |
| 2011/0144427 A1 | 6/2011 | Morningstar et al. |
| 2011/0144428 A1 | 6/2011 | Morningstar et al. |
| 2012/0184806 A1 | 7/2012 | Daniel |

FOREIGN PATENT DOCUMENTS

| | | |
|---|---|---|
| CN | 2127302 Y | 2/1993 |
| CN | 2168565 Y | 6/1994 |
| CN | 2464274 Y | 12/2001 |
| CN | 1328809 A | 1/2002 |
| CN | 1341406 A | 3/2002 |
| CN | 1859882 A | 11/2006 |
| CN | 1893894 A | 1/2007 |
| EP | 0682923 A1 | 11/1995 |
| GB | 2163354 A1 | 2/1986 |
| JP | 2009131310 A2 | 6/2009 |
| WO | 0167996 A2 | 9/2001 |
| WO | 03071970 A1 | 9/2003 |
| WO | 2004045421 A1 | 6/2004 |
| WO | 2008008547 A2 | 1/2008 |
| WO | 2011035787 A1 | 3/2011 |

* cited by examiner

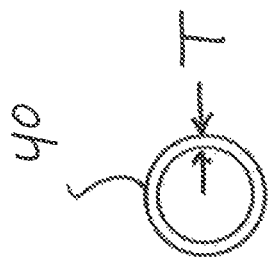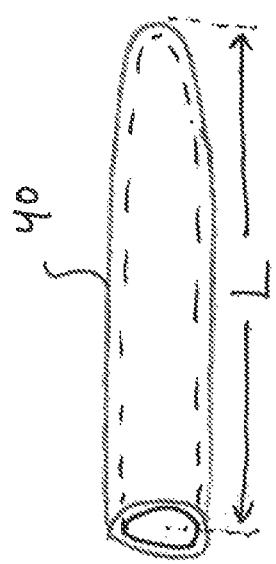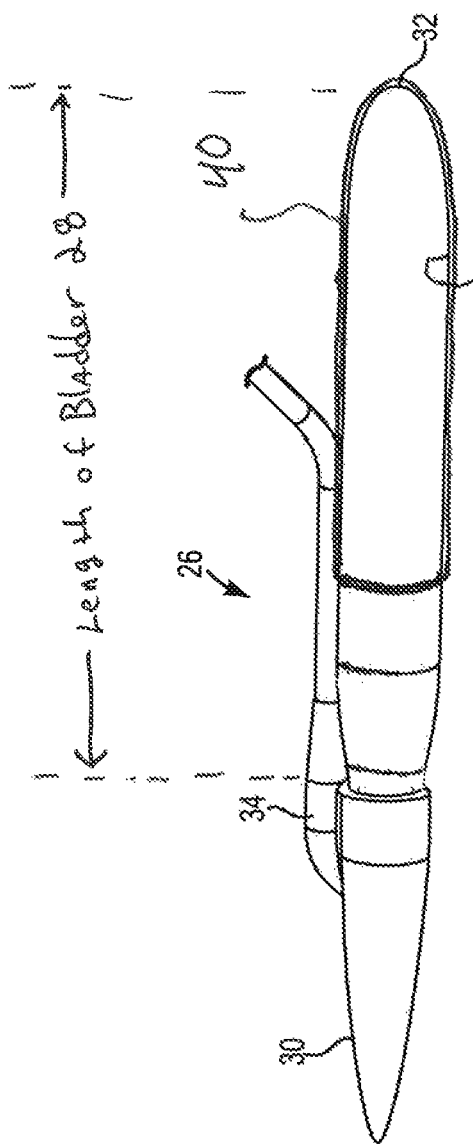

PENILE PROSTHETIC WITH AN INSERTION SLEEVE ATTACHABLE TO AN INFLATABLE BLADDER

SUMMARY

One aspect provides a penile implant having a proximal tip that is insertable into a crus penis, an inflatable bladder having a distal tip that is insertable into a glans penis, with the inflatable bladder sealed to the proximal tip, and an insertion sleeve attachable over the inflatable bladder. The insertion sleeve dissolves after implantation of the penile implant into a patient.

The insertion sleeve allows the surgeon to push the penile implant into the penis without the use of secondary tools, such as a Furlow device or a Keith needle.

The insertion sleeve provides the penile implant with sufficient rigidity to allow the penile implant to be inserted into a corporotomy and subsequently pushed in a distal direction into the glans penis. In the presence of liquid, for example during irrigation or body fluids after implantation, the insertion sleeve dissolves and is absorbed by the body.

One aspect provides a method of implanting a penile prosthetic including:
  forming an incision in skin of a penis;
  exposing a corpora cavernosum of the penis;
  inserting an insertion sleeve into the corpora cavernosum of the penis, where the insertion sleeve is dissolvable in water;
  inserting a penile implant into the insertion sleeve; and
  closing the incision in the skin of the penis.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 2 is a perspective view of an insertion sleeve.

FIG. 3 is an end view of an insertion sleeve.

FIG. 4 is a side view of the insertion sleeve illustrated in FIGS. 2 and 3 attached to an inflatable bladder of the penile implant.

DETAILED DESCRIPTION

Figure 1:
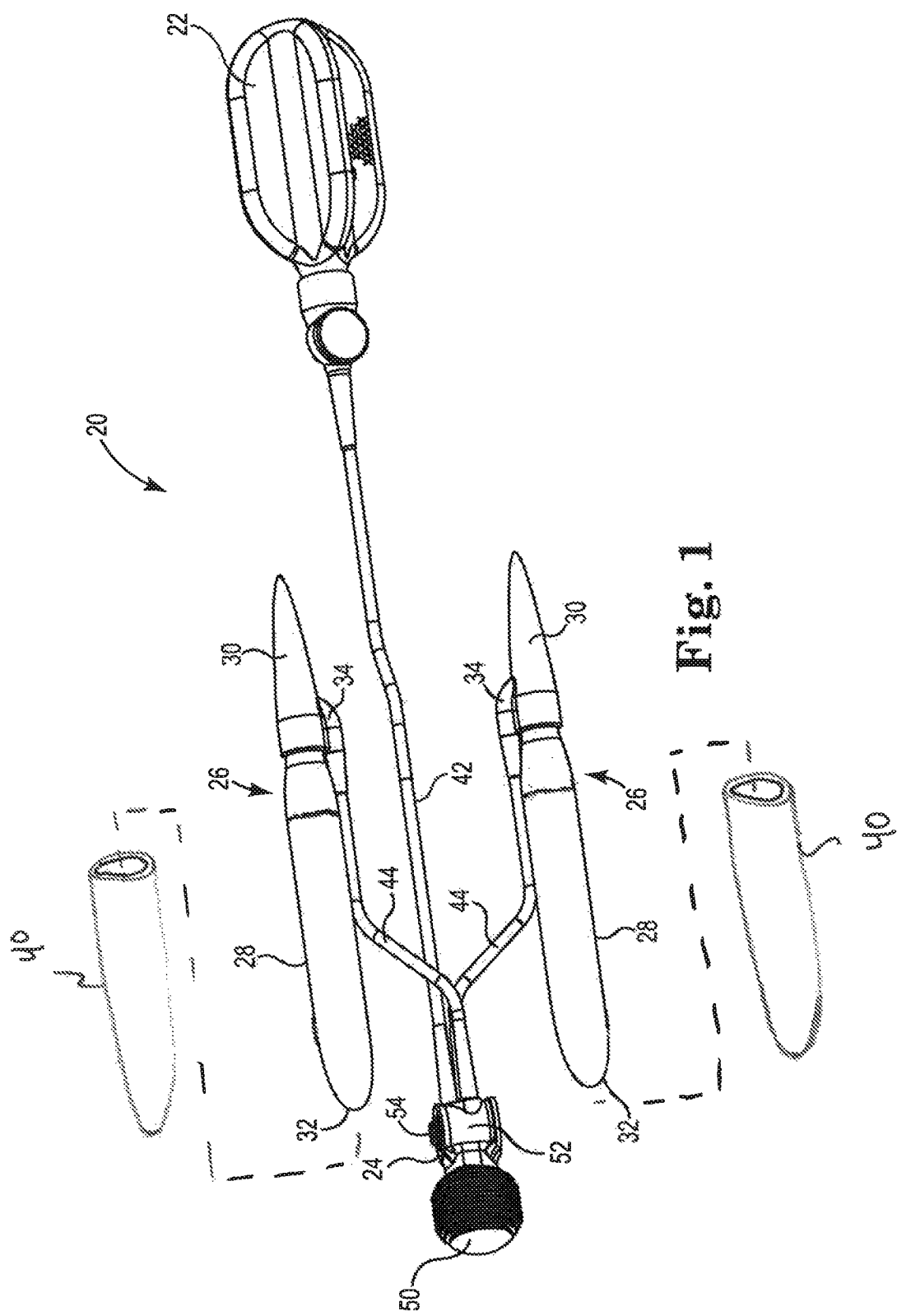
FIG. 1 is a perspective view of one embodiment of a penile prosthetic including a pump connected to two penile implants, a reservoir, and insertion sleeves attachable to the penile implants.

In the following detailed description, reference is made to the accompanying drawings. The drawings form a part of this specification and illustrate exemplary embodiments for practicing the invention. Directional terminology, such as "top," "bottom," "front," "back," "leading," "trailing," etc., is used with reference to the orientation of the Figure(s) being described. Because components of embodiments can be positioned in a number of orientations, the directional terminology is used for purposes of illustration and is in no way limiting. It is to be understood that other embodiments may be utilized and structural or logical changes may be made without departing from the scope of the invention. The detailed description describes examples for practicing the invention and is not to be read to limit the scope of the invention. The scope of the invention is defined by the attached claims.

Embodiments, and features of the various exemplary embodiments described in this application, may be combined with each other ("mixed and matched"), unless specifically noted otherwise.

End means endmost. Relative to an observer, for example a surgeon, a distal end is the furthest endmost location of a distal portion of a thing being described, whereas a proximal end is the nearest endmost location of a proximal portion of the thing being described. The portion next to or adjacent to an end is an end portion.

An implanted penile prosthetic has proven useful in treating erectile dysfunction in men. One acceptable implanted penile prosthetic includes two inflatable cylinders implanted in the penis, a pump implanted in the scrotum or other internal space of the body, and a liquid holding reservoir implanted in the abdomen or other internal space of the body, with the pump connected to the cylinders and the reservoir.

In an implantation procedure, the penis of the patient is incised in a corporotomy to expose a pair of corpora cavernosa that are aligned axially in a side-by-side orientation within the penis. A cutting implement, such as a curved Mayo scissors, is employed to penetrate the fascia of the penis and form an opening accessing each corpora cavernosum. Subsequently, each corpora cavernosum is dilated (opened) with an appropriate dilation tool to form a recess that is sized to receive one of the two cylinders of the penile prosthetic.

Thereafter, a tool (referred to by surgical practitioners as a "Furlow" introducer) is inserted into each dilated corpora cavernosum to measure a length of the penis distally and proximally to determine a desired length of the cylinders to be implanted. A cylinder of the appropriately selected length is secured to a suture, and the suture is secured to a needle (sometimes called a "Keith" needle). The Keith needle is attached to the Furlow introducer. The Keith needle could possibly fall out of the Furlow introducer, so the surgical staff handles the tool with care. The surgeon inserts the Furlow introducer into the dilated corpora cavernosum. The surgeon steadies the Furlow introducer with one hand and pushes a plunger (or obturator) of the Furlow introducer with the other hand. Pushing the plunger pushes the needle from of the introducer, through tissue of the penis, and out the glans penis. The exposed portion of the needle is handled by the surgeon, removed from the suture, and discarded. The remaining suture is subsequently employed to tow the cylinder into place within the dilated corpora cavernosum.

The above-described procedure has proven effective when implanting penile prostheses. However, surgeons would appreciate having fewer parts to handle during the procedure. In addition, surgeons and those handling the Keith needle would possibly welcome an approach for implanting a penile prosthetic that reduces or eliminates their exposure to the Keith needle.

This disclosure describes several embodiments that address the problem of the Keith needle falling out of a Furlow tool during the procedure and the surgeon handling a variety of components including a needle, a suture, and a Furlow tool by providing a solution where an insertion sleeve is attached to an outside surface of a penile implant to provide an effective column strength allowing insertion of the implant into the penis without external tools, needles, or sutures.

One embodiment provides a penile prosthetic having an insertion sleeve attachable to the outside surface of an inflatable penile implant. The inflatable penile implant is sized for insertion into a dilated corpora cavernosum of a penis and includes a proximal tip that is insertable into the crus penis and a bladder connected to the proximal tip. The bladder includes a distal tip that is insertable into the glans penis. The insertion sleeve provides the bladder with a column strength that is sufficient for insertion of the bladder into the dilated corpora cavernosum of the penis. The insertion sleeve dissolves and is absorbed by the body after implantation of the penile implant and closure of the corporotomy.

A column strength that is sufficient for insertion of the penile implant into the dilated corpora cavernosum of the penis is a column strength that is stronger than a column strength of the bladder portion of a penile implant. For example, an inflatable penile implant is provided with a soft and pliable inflatable bladder connected to a proximal tip. While the proximal tip is harder and stronger than the rest of the penile implant (to support the implant against the bony structure of the crus penis), the implant has a column strength associated with the least strong component, which is the bladder. The soft and pliable bladder has a column strength in a range from about 4-12 ounces (about one-quarter to about three-quarters of a pound force). The bladder is designed to be compliant when deflated so that the penis is naturally flaccid when the implant is not erect. A consequence of the pliability is that the column strength of the bladder is insufficient to allow the bladder to be pushed into the dilated corpora cavernosum during implantation. For this reason, the bladder is typically towed into position by a Furlow needle attached to a length of suture. The Furlow needle pierces the glans penis and the suture tows the bladder into the dilated corpora cavernosum.

A column strength that is sufficient for insertion of the penile implant into the dilated corpora cavernosum of the penis is a column strength of about 1 pound force or greater, with a realistic upper limit for the column strength being about 20 pounds force. One useful column strength for the penile implant as provided by the insertion sleeve is in a range from 1-10 pounds force. While the column strength can be larger than 10 pounds force, a surgeon will generally back off from pushing with more than 10 pounds force and inspect the cavity (corpora cavernosum in the distal direction and the dilated crus in the proximal direction) to determine why resistance is being met.

One embodiment provides a penile prosthetic having a penile implant sized for insertion into a dilated corpora cavernosum of a penis, and an insertion sleeve attachable to an outside surface of the penile implant. The insertion sleeve is fabricated from a gelling agent that is configured to dissolve in water.

One embodiment provides a penile prosthetic having a penile implant sized for insertion into a dilated corpora cavernosum of a penis, and an insertion sleeve attachable to an outside surface of the penile implant. The insertion sleeve dissolvable in an aqueous liquid having a temperature in a range from 70-100 degrees Fahrenheit.

One embodiment provides a penile prosthetic having a penile implant sized for insertion into a dilated corpora cavernosum of a penis, and an insertion sleeve attachable to an outside surface of the penile implant. The insertion sleeve is formed from one or more of, or combinations of a starch, polysaccharides, derivatives of polysaccharides, sugar, simple sugars, fructose, derivatives of fructose, modified forms of starch, or modified forms of starch and cellulose.

One embodiment provides a penile prosthetic having a penile implant sized for insertion into a dilated corpora cavernosum of a penis, and an insertion sleeve attachable to an outside surface of the penile implant. The insertion sleeve is formed from one of a gelatin, a collagen, or a carrageenan.

One embodiment provides a penile prosthetic having a penile implant provided as an inflatable bladder that is sized for insertion into a dilated corpora cavernosum of a penis, and an insertion sleeve attachable to an outside surface of the penile implant. The inflatable bladder has a first column strength in a range from ¼-¾ pounds force, and the insertion sleeve provides the penile implant with an effective column strength in a range from 1-10 pounds force.

One embodiment provides a penile prosthetic having a penile implant sized for insertion into a dilated corpora cavernosum of a penis, and an insertion sleeve attachable to an outside surface of the penile implant. The insertion sleeve has a durometer in a range from 40 Shore A to 70 Shore A.

One embodiment provides a penile prosthetic having an insertion sleeve attachable to the outside surface of an inflatable penile implant. The inflatable penile implant is sized for insertion into a dilated corpora cavernosum of a penis and includes a proximal tip that is insertable into the crus penis and a bladder connected to the proximal tip. The bladder includes a distal tip that is insertable into the glans penis. The insertion sleeve provides the bladder with a column strength that is sufficient for insertion of the bladder into the dilated corpora cavernosum of the penis. The proximal tip has a durometer in a range from 40 Shore A to 70 Shore A and the distal tip is softer than the proximal tip and has a durometer in a range from 0 Shore A to 39 Shore A.

FIG. 1 is a perspective view of one embodiment of an implantable penile prosthetic 20. The penile prosthetic 20 includes a reservoir 22 sized to contain a volume of liquid, a pump 24 connected to the reservoir 22 and operable to move the liquid out from the reservoir 22 and back into the reservoir 22, and a pair of penile implants 26, where one each of the penile implants 26 is body implantable in a corpora cavernosum of a penis. Each penile implant 26 includes a bladder 28 permanently attached to a proximal tip 30. The bladder 28 is inflatable with the liquid from the reservoir 22 and includes a closed distal tip 32 that is insertable into the glans penis, and the proximal tip 30 is insertable into the crus penis and includes a tubing port 34 communicating between the bladder 28 and the pump 24. An insertion sleeve 40 is provided that is sized to be attached over each of the bladders 28.

The reservoir 22 is attachable intra-operatively to the pump 24 by tubing 42, and the pump 24 is attachable intra-operatively to each penile implant 26 by separate tubing 44.

The components (the reservoir 22, the pump 24, the implants 26, the sleeves 40, and the tubing 42, 44) of the penile prosthetic 20 are generally provided unassembled in a kit of parts. The components are assembled immediately prior to surgery, or intra-operatively, as determined by the surgeon. For example, each sleeve 40 is slid into a respective one of the expanded corpora cavernosa. Each of the tubing lengths 42, 44 have a portion that is attached to the reservoir 22 and a portion that is attached to the implants 26, respectively, and a portion that is secured to the pump 24. The bladder 28 is pushed into the sleeve 40 that has been inserted in the corpora cavernosum. In some embodiments, the bladder 28 includes a friction reducing coating, or a lubricant, to assist in sliding the bladder 28 into the inserted sleeve 40. The tubing lengths are connected intra-operatively with some form of tubing connector useful with surgical implants. The components of the penile prosthetic 20 are illustrated in an assembled configuration in FIG. 1.

The reservoir 22 is sized for implantation within the human body, for example within the abdomen. The reservoir 22 is sized to retain a volume of liquid useful in inflating the inflatable bladders 28, for example with a volume in a range from 50-350 cc. One useful size of reservoir 22 contains about 200 mL of liquid. The liquid is aqueous based. During some procedures the liquid is water, and during other procedures the liquid is saline, depending upon the preference of the surgeon. Suitable materials for fabricating the reservoir 22 include silicone, polymers such as urethanes, a blend of polymers with urethane, copolymers of urethane, or the like. In one exemplary fabrication process, one of the suitable materials identified above is molded into a container shape appropriate for implantation in the space of Retzius or in the abdomen.

The pump 24 includes a pump bulb 50 connected to a pump housing 52. The pump bulb 50 is pliant and configured to be repeatedly squeezed by the user of the prosthetic 20 to move liquid into and out of the implants 26. The pump housing 52 contains the valving that operates to allow a one-way flow of liquid from the reservoir 22 to the inflatable bladders 28 in response to a squeezing of the pump bulb 50, and a one-way flow of liquid out of the inflatable bladders 28 back to the reservoir 22 in response to a touch of the deflation button 54.

The penile implants 26 are sized to be implanted into the penis. Each of the penile implants 26 includes one inflatable bladder 28 that is sealed or attached to the proximal tip 30. The inflatable bladders 28 are fabricated from material configured to be flexible when deflated to provide the penis with a natural, flaccid state and expand when inflated with liquid to provide the penis with an erect state. Suitable material for fabricating the inflatable bladders 28 includes silicone, polymers such as urethanes, a blend of polymers with urethane, copolymers of urethane, or the like. Suitable penile implants 26 are available from Coloplast Corp., Minneapolis, Minn.

The inflatable bladder 28 is a thin-walled balloon-like tube made of a soft polymer. The distal tip 32 is sealed closed. The inflatable bladder 28 is suitably manufactured in a molding process or other process to fabricate a thin and substantially uniform wall thickness that forms an internal cavity. The style of penile implant that is implanted with a Keith needle and a Furlow device has a reinforced/strengthened distal tip that allows the implant to be towed into place by a suture that is inserted through a hole in the distal tip of the implant. Such a reinforced distal tip potentially has an unnaturally hard configuration that can feel cold or potentially "unnatural" when implanted in a penis. In contrast, the inflatable bladder 28 may be fabricated to include a uniform wall thickness such that the distal tip 32 is uniformly thin, more compliant, and possibly more natural feeling than an implant with a reinforced tip.

In one embodiment, the proximal tip 30 has a durometer in a range from 40 Shore A to 70 Shore A and the distal tip 32 is softer than the proximal tip 30 and has a durometer in a range from 0 Shore A to 39 Shore A. The proximal tip 30 is formed of a hardened material adapted to brace against the bony crus penis within the pelvis. The soft distal tip 32 is implanted in the glans penis and is both flexible and pliant to provide the user with a natural-feeling penis tip. The penile implant 26 does away with the use of the Keith needle, and thus does away with the hole formed in the distal tip. Prior devices that have a hole in the distal tip to accommodate the suture that pulls the Keith needle are associated with a harder distal tip that might possibly be less natural feeling to the user. The penile implant 26 allows for crafting the desired and improved shape of the distal tip 32 and is characterized by an absence of a suture tow hole and is noticeably softer than the distal tip of prior devices.

FIG. 2 is a side view of the insertion sleeve 40, FIG. 3 is an end view of the insertion sleeve 40, and FIG. 4 is a side view of the insertion sleeve 40 placed over the bladder 28.

In one embodiment, the insertion sleeve 40 has a length L that is longer than the length of the bladder 28. In one embodiment, the insertion sleeve 40 has a length L that is the same as the length of the bladder 28. In one embodiment, the insertion sleeve 40 has a length L that is less than the length of the bladder 28. In one exemplary embodiment, the insertion sleeve 40 has a length that is about 75% the length of the bladder 28, which allows the surgeon to grasp the implant 28 on the bladder potion that is not covered by the sleeve 40.

The insertion sleeve 40 has a thickness T selected to configure the insertion sleeve 40 to dissolve within 24 hours after implantation, preferably within 4 hours after implantation. In one embodiment, the insertion sleeve 40 has a thickness T in a range from 0.008 inches to 0.020 inches, and preferably about 0.015 inches. The thickness is proportional to the time for dissolution of the sleeve 40, so the thickness of the sleeve depends upon the concentration of the gelling agent in solution and upon the selection of the gelling agent.

In one embodiment, the insertion sleeve 40 is inserted into the dilated corpora of the penis and the bladder 28 of the implant 26 is subsequently inserted into the sleeve 40.

In one embodiment, the insertion sleeve 40 is placed over the bladder 28 of the implant 26 and this combination is subsequently inserted into the dilated corpora of the penis.

The insertion sleeve 40 is placed over the inflatable bladder 28 to provide the penile implant 26 with an increased column strength. The increased column strength is useful to allow the surgeon to push the assembled penile implant 26 into a dilated corpora cavernosum of the penis. It is desirable that the penile implant 26 have a sufficient column strength to allow the surgeon to push the implant 26 into the penis during an implantation procedure. However, it is also desirable that the increased column strength associated with the penile implant 26 can be removed or otherwise reduced to allow the implant 26 to occupy a natural, flaccid penis state. Embodiments provide examples of insertion sleeves that have a sufficient column strength to allow the surgeon to insert the cylinder into a corpora cavernosum during an implantation procedure, where the insertion sleeve is configured to dissolve or disassociate or lose its column strength within about 60-120 minutes, preferably 30-60 minutes after implantation or exposure to an aqueous liquid. This allows for a stiff insertion sleeve during insertion and a flaccid insertion sleeve minutes after implantation.

In one embodiment, the insertion sleeve 40 is fabricated from a material that dissolves in the presence of an aqueous liquid such as water or saline. One such insertion sleeve 40 is dissolvable in water having a temperature in a range from 70-100 degrees Fahrenheit.

In one embodiment, the insertion sleeve 40 is fabricated as a cylinder from an aqueous solution of a gelling agent derived from animal protein, a gelatin, collagen, plant polysaccharides or their derivatives like carrageenan, or modified forms of starch and cellulose. Suitable insertion sleeves 40 are fabricated from starch, polysaccharides, derivatives of polysaccharides, sugar, simple sugars, fructose or derivatives of fructose, modified forms of starch, or modified forms of starch and cellulose. Insertion sleeves fabricated from such materials will dissolve when exposed to water. The gelling agent can include additives like plasticizers, glycerin, sorbitol, coloring agents, preservatives, or lubricants. The gelling agent is coated onto a mandrel in the shape of the bladder 28, for example, and allowed to harden into the sleeve 40. The hardened sleeve 40 is removed from the mandrel and has an increased column strength over the bladder 28 alone, and an increased column strength over a penile implant without the insertion sleeve 40. The insertion sleeve 40 is adapted to go into solution and is absorbed into the body and is imperceptible to the user.

Figure 5:
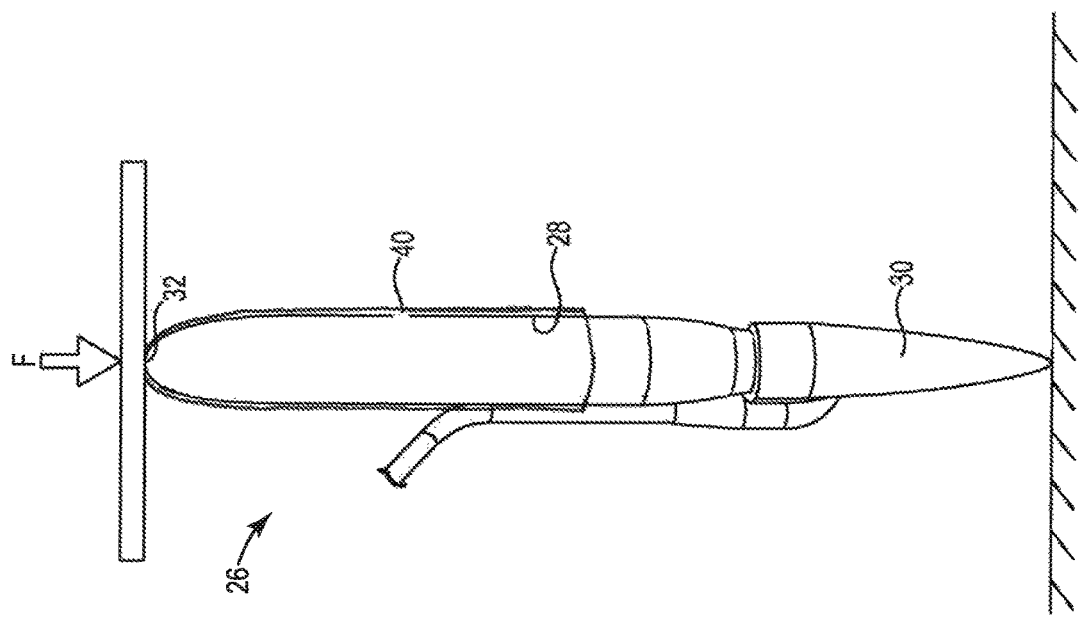
FIG. 5 is a schematic view of one of the penile implants illustrated in FIG. 1 demonstrating the insertion sleeve providing the penile implant with increased column strength.

FIG. 5 is a schematic view of the insertion sleeve 40 providing the implant 26 with increased column strength. The implant 26 is inserted between opposing rams of a testing device. A force F is applied to one of the movable rams to apply an axial force to the implant 26. Absent the insertion sleeve 40, a penile implant will support a column force F of less than 1 pound before buckling under load. With the insertion sleeve 40, the portion of the bladder 28 that is covered by the sleeve 40 is provided with an effective column strength, which is a column strength above 1 pound force, with a working example of the implant 26 having a range of column strength from 1-20 pounds force. One suitable effective column strength for the implant 26 provided with the insertion sleeve 40 is an effective column strength in a range from 1.25-10 pounds force.

In one embodiment, the insertion sleeve 40 has a durometer in a range from 40 Shore A to 70 Shore A prior to exposure to an aqueous liquid.

Figure 6:
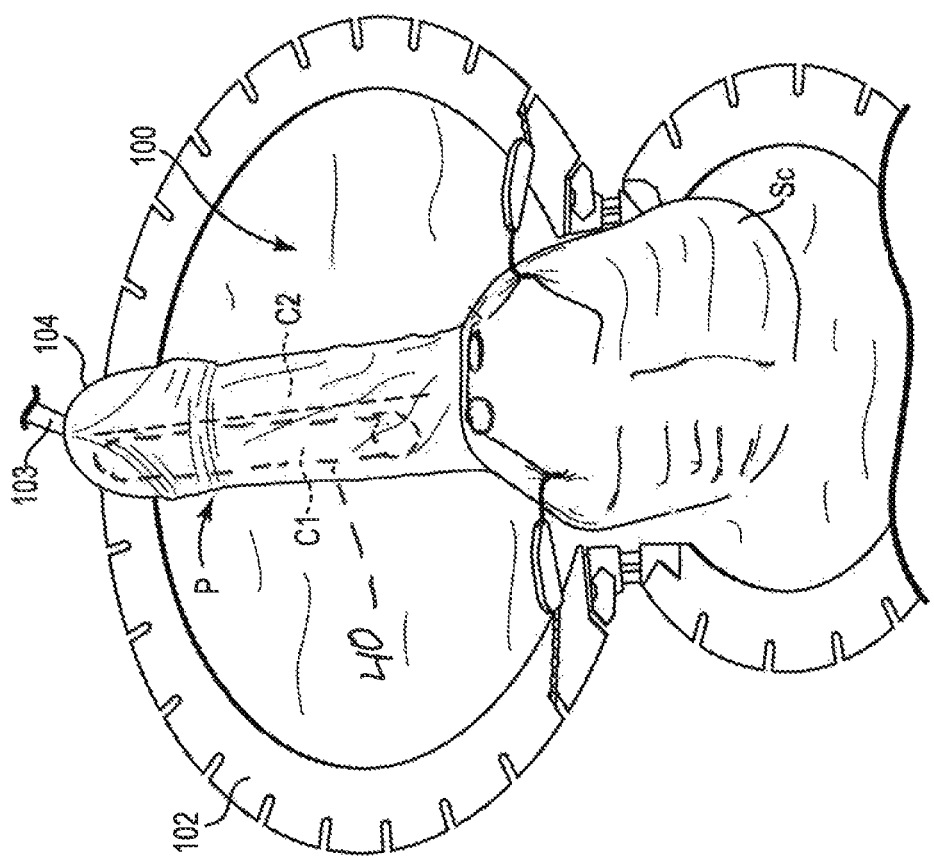
FIGS. 6-8 are schematic views of an implantation procedure for placement of the penile implants illustrated in FIG. 1 into a penis.
Figure 7:
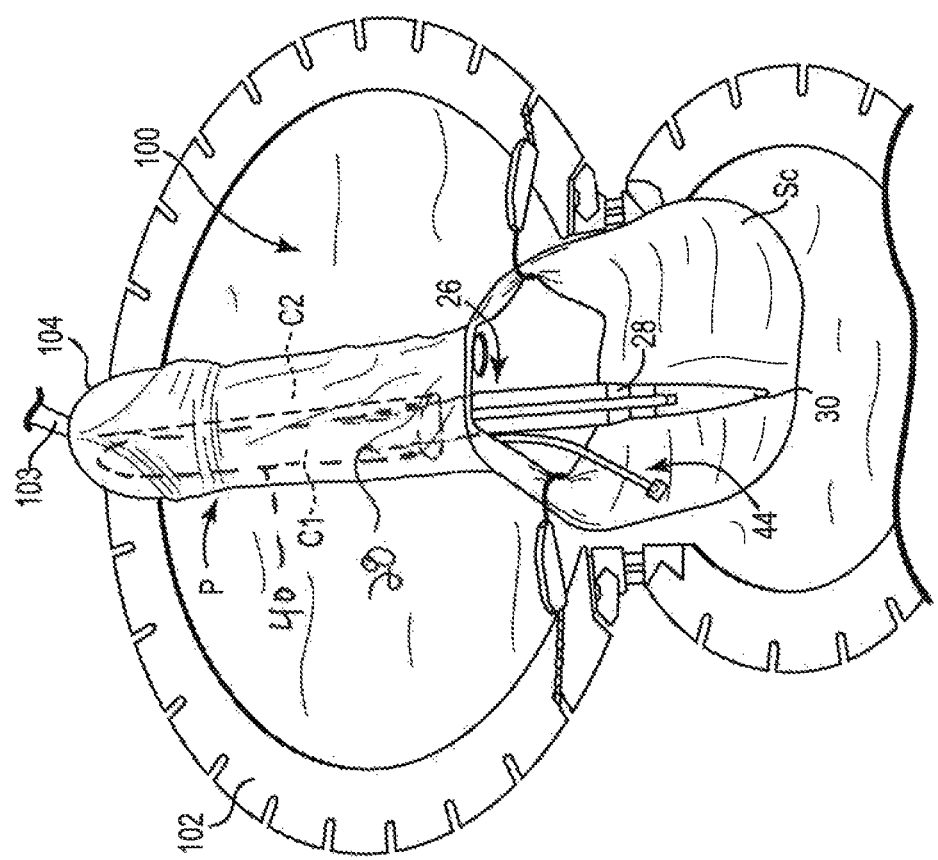
Figure 8:
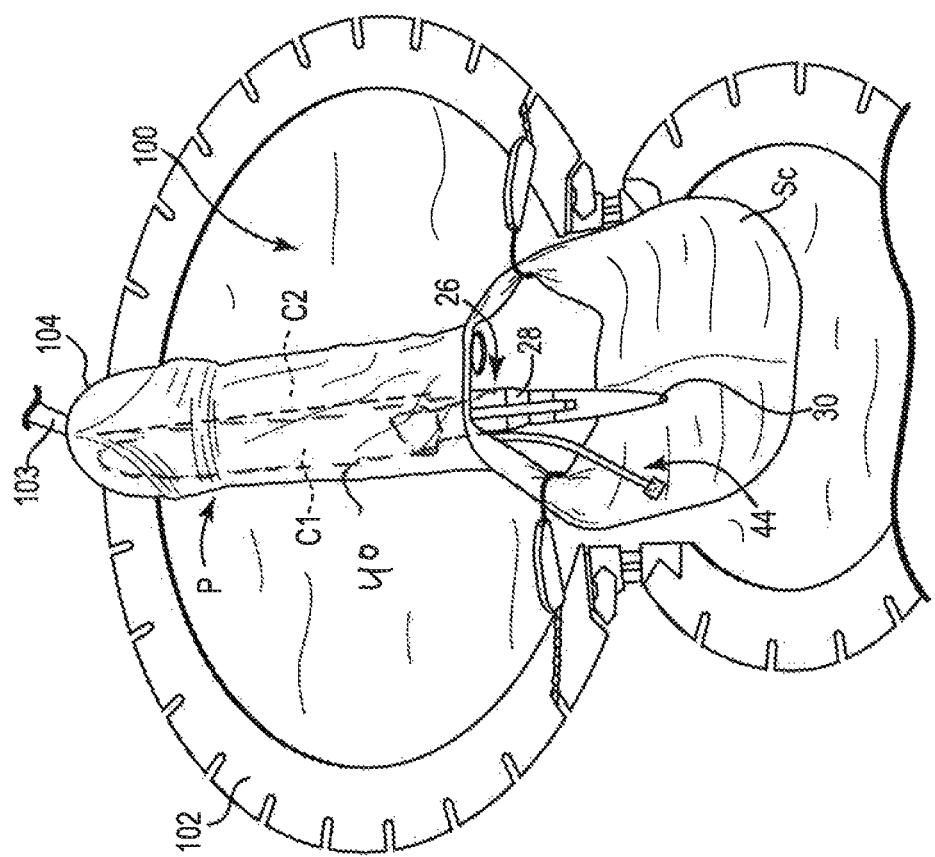

FIG. 6, FIG. 7, and FIG. 8 are schematic views of an implantation procedure for the penile implant 26.

The groin area 100 of the patient is shaved, cleaned and suitably prepped with a surgical solution prior to draping with a sterile drape as directed by the healthcare provider's procedures. A retraction device 102, such as those available from Lone Star Medical Products of Stafford, Tex., is placed around the penis P if so desired by the surgeon to establish the surgical field. A catheter 103 is inserted into the urethra U from the distal end 104 of the penis P. The penis P is reclined against the torso and incised to expose the corpora cavernosa (C1 and C2).

Suitable examples of incisions include either an infrapubic incision or a transverse scrotal incision. The infrapubic incision is initiated between the umbilicus and the penis (i.e., above the penis), whereas the transverse scrotal incision is made across an upper portion of the patient's scrotum Sc.

As an example of the transverse scrotal approach, the surgeon forms a 2-3 cm transverse incision through the subcutaneous tissue of the median raphe of the upper scrotum Sc and dissects down through the Darto's fascia and Buck's fascia to expose the tunicae albuginea of the penis P. Thereafter, each corpora cavernosum C1 and C2 is exposed in a corporotomy where a small (approximately 1.5 cm) incision is formed to allow the surgeon to access and subsequently dilate the corpora cavernosa C1 and C2.

The surgeon typically will insert a blunt-ended scissors or other elongated sleeve to separate a portion of the spongiosum material to open a pathway for dilation and measurement of the corpora cavernosum C1, C2. After suitable dilation, the surgeon measures the length of the corpora cavernosa to determine the suitable size for the penile implant 26. In one approach, the surgeon ensures that the appropriately sized penile implant 26 has been selected by measuring the proximal and distal length of each corpora cavernosum C1 and C2. For example, a ruler is inserted into one of the corpora cavernosa C1 or C2 forward in the distal penis toward the glans penis, the distal measurement is recorded by reading the ruler, and the ruler is inserted into the same corpora cavernosa C1 or C2 rearward in the proximal penis toward the crus of the penis to record the proximal length of the corpora by reading the ruler. The distal and proximal measurements would typically be made in reference to a "stay stitch" temporarily placed in the incision. The sum of the distal and the proximal measurements represent the length of that corpora cavernosum, and this information is employed to select a size of the penile implant 26. This procedure is repeated for the other of the corpora cavernosa C1 or C2 to ensure the appropriately sized penile implant 26 has been selected for the companion corpora.

FIG. 6 is a schematic view after the surgeon has pushed the of the insertion sleeve 40 into the corpora cavernosum C1, for example with a finger or with a blunt cavernatome tool.

FIG. 7 is a schematic view of the implant 26 partially inserted into the insertion sleeve 40. Some implants include a hydrophilic coating. When wetted with water, the hydrophilic coating makes the bladder 28 slippery and easily insertable into the insertion sleeve 40.

FIG. 8 is a schematic view of the implant 26 fully inserted and seated into the insertion sleeve 40.

A similar implantation procedure is performed as the second penile implant 26 is inserted into the second corpora cavernosum C2.

The surgeon connects the tubing between the reservoir 22, the pump 24, and the implants 26 (see FIG. 1) and confirms that the penile prosthetic 20 is operating appropriately. The incision is closed. No Keith needle has been employed and no tow suture was used to place the implant 26 in the penis.

In one embodiment, the implant includes a hydrophilic coating, for example on at least the bladder 28 portion. Wetting the hydrophilic coating on the exterior surface of the penile implant provides the penile implant with a lubricated surface, which allows the surgeon to slide the lubricated surface of the penile implant into the insertion sleeve.

In another approach, the sleeve 40 is placed over the bladder 28 prior to inserting the combined sleeve 40 and the bladder 28 into the dilated corpora cavernosum C1. The insertion sleeve 40 provides the penile implant 26 with a column strength that is sufficient to allow the surgeon to push the penile implant 26 in a distal direction to the distal end 104 of the penis. The surgeon would typically grasp the bladder 28 immediately proximal of the sleeve 40 prior to inserting the sleeve 40 and the bladder 28 into the penis. In the presence of irrigation liquid or body fluid the insertion sleeve 40 softens, dissolves, disassociates, or otherwise is absorbable into the body after implantation. The surgeon subsequently places the proximal end 30 of the implant 26 into the crus penis.

Embodiments of the penile prosthetic include an insertion sleeve that is dissolvable in water or an aqueous liquid, which advantageously allows the insertion sleeve to soften or dissolve after having provided the implant with an effective column strength that allows the surgeon to implant the device without a Keith needle or tow suture.

Embodiments of the penile prosthetic include an insertion sleeve that is dissolvable in an aqueous liquid having a temperature in a range from 70-100 degrees Fahrenheit, which advantageously allows the insertion sleeve to dissolve after implantation in the human body.

Embodiments of the penile prosthetic include an insertion sleeve formed from a gelatin, a collagen, a carrageenan, a starch, polysaccharides, derivatives of polysaccharides, sugar, simple sugars, fructose, derivatives of fructose, modified forms of starch, or modified forms of starch and cellulose. Such an insertion sleeve is rigid and strong when dry to advantageously allow insertion of the implant into the penis, and dissociates or dissolves when exposed to an aqueous liquid.

Embodiments of the penile prosthetic include an insertion sleeve with an increased effective column strength relative to the bladder, which advantageously provides the implant with an implantation column strength in a range from 1-10 pounds force to allow implantation without a Keith needle or tow suture.

Embodiments of the penile prosthetic include an insertion sleeve with a durometer in a range from 40 Shore A to 70 Shore A, which advantageously provides the implant with an implantation column strength in a range from 1-10 pounds force to allow implantation without a Keith needle or tow suture.

Although specific embodiments have been illustrated and described, it will be appreciated by those of ordinary skill in the art that a variety of alternate and equivalent implementations may be substituted for the specific embodiments shown and described without departing from the scope of the present invention. This application is intended to cover any adaptations or variations of the kind of medical devices described above. Therefore, it is intended that this invention be limited only by the claims and their equivalents.

What is claimed is:

1. A penile prosthetic comprising:
a penile implant sized for insertion into a dilated corpora cavernosum of a penis, the penile implant includes a proximal tip that is insertable into a crus penis and an inflatable bladder connected to the proximal tip, the inflatable bladder has a distal tip that is insertable into a glans penis; and
an insertion sleeve having a sleeve wall extending from an opening formed in a proximal end of the insertion sleeve to a closed distal end of the insertion sleeve, with the closed distal end of the insertion sleeve configured to enclose the distal tip of the inflatable bladder when the insertion sleeve is attached over an outside surface of the inflatable bladder;
wherein the insertion sleeve is soluble in one of water and saline.

2. The penile prosthetic of claim 1, wherein the insertion sleeve is dissolvable in an aqueous liquid having a temperature in a range from 70-100 degrees Fahrenheit.

3. The penile prosthetic of claim 1, wherein the insertion sleeve is formed from a material selected from a group consisting of starch, polysaccharides, derivatives of polysaccharides, sugar, simple sugars, fructose, derivatives of fructose, and a combination of starch and cellulose.

4. The penile prosthetic of claim 1, wherein the insertion sleeve is formed from one of a gelatin, a collagen, and a carrageenan.

5. The penile prosthetic of claim 1, wherein the inflatable bladder has a first column strength in a range from ¼-¾ pounds force, and the insertion sleeve provides the penile implant with an effective column strength in a range from 1-10 pounds force.

6. The penile prosthetic of claim 1, wherein the insertion sleeve has a durometer in a range from 40 Shore A to 70 Shore A.

7. The penile prosthetic of claim 1, wherein the proximal tip has a durometer in a range from 40 Shore A to 70 Shore A and the distal tip is softer than the proximal tip and has a durometer in a range from 0 Shore A to 39 Shore A.

8. A method of implanting a penile prosthetic, the method comprising:
forming an incision in skin of a penis;
exposing a corpora cavernosum of the penis;
inserting an insertion sleeve into the corpora cavernosum of the penis, where the insertion sleeve is dissolvable in an aqueous liquid;
inserting a penile implant into the insertion sleeve; and
closing the incision in the skin of the penis.

9. The method of claim 8, further comprising wetting a hydrophilic coating on an exterior surface of the penile implant providing the penile implant with a lubricated surface; and
sliding the lubricated surface of the penile implant into the insertion sleeve.

10. The method of claim 8, further comprising irrigating the insertion sleeve and sliding the penile implant into the insertion sleeve.

11. The penile prosthetic of claim 1, wherein the insertion sleeve is adapted insert the penile implant into the dilated corpora cavernosum of the penis without a suture.

12. The penile prosthetic of claim 1, wherein the insertion sleeve is adapted insert the penile implant into the dilated corpora cavernosum of the penis without a suture and without an external insertion tool.

* * * * *